US00PP31500P2

(12) United States Plant Patent
Egger

(10) Patent No.: US PP31,500 P2
(45) Date of Patent: Feb. 25, 2020

(54) ***PENSTEMON* PLANT NAMED 'TNPENHPI'**

(50) Latin Name: ***Penstemon* hybrid**
Varietal Denomination: TNPENHPI

(71) Applicant: Terra Nova Nurseries, Inc., Canby, OR (US)

(72) Inventor: Janet N. Egger, Seattle, WA (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 16/350,951

(22) Filed: Feb. 4, 2019

(51) Int. Cl.
*A01H 5/02* (2018.01)
*A01H 6/68* (2018.01)

(52) U.S. Cl.
USPC ..... Plt./465
CPC ..... *A01H 6/68* (2018.05)

(58) Field of Classification Search
USPC ..... Plt./465
See application file for complete search history.

*Primary Examiner* — Anne Marie Grunberg
(74) *Attorney, Agent, or Firm* — Klarquist Sparkman, LLP

(57) ABSTRACT

A new and distinct *Penstemon* plant characterized by medium-size flowers; pink flowers with white throats; long bloom time; good rebloom; compact, upright, well-branched habit with multiple crowns from the base; and excellent vigor.

1 Drawing Sheet

Botanical denomination: *Penstemon* hybrid.
Variety designation: 'TNPENHPI'.

BACKGROUND OF THE INVENTION

The present invention relates to a new and distinct *Penstemon* plant given the name 'TNPENHPI'. *Penstemon* is in the family Scrophulariaceae. *Penstemon* 'TNPENHPI' originated from open-pollinated seeds of *Penstemon* '261-1', an unnamed, unpatented, proprietary plant. It was part of a controlled breeding program to create a compact, upright, medium-small size, reblooming, and hardy series. This seedling was selected for its medium size pink flowers with white throats, flowers in dense clusters, long bloom time, good rebloom, vigor, and clean, attractive look. It is an ideal plant for a sunny border in full sun.

SUMMARY OF THE INVENTION

The present invention has not been evaluated under all possible environmental conditions. The phenotype may vary with variations in environment without a change in the genotype of the plant.

*Penstemon* 'TNPENHPI' is uniquely distinguished by its:

1. medium-size flowers,
2. pink flowers with white throats,
3. long bloom time,
4. good rebloom,
5. compact, upright, well-branched habit with multiple crowns from the base, and
6. excellent vigor.

Compared to the seed parent, *Penstemon* '261-1', the new plant has a more upright habit, rather than floppy habit, and light pink flowers, rather than dark pink flowers.

Compared to *Penstemon* Rock Candy™ Pink 'Novapenpin' (U.S. Plant Pat. No. 26,701), the new plant is lighter pink, rather than magenta, and has white bee tracks and throat.

Compared to *Penstemon* 'Cha Cha Pink' (U.S. Plant Pat. No. 26,673), the new plant is shorter, smaller and narrower leaves, light pink flowers rather than dark pink, and smaller flowers.

Trade Designation: HARLEQUIN™ Pink.

The new variety has been reproduced only by asexual propagation (cuttings and micropropagation). Each of the progeny exhibits identical characteristics to the original plant. Asexual propagation by cuttings and micropropagation using terminal and lateral shoots as done in Canby, Oreg., shows that the foregoing characteristics and distinctions come true to form and are established and transmitted through succeeding propagations.

BRIEF DESCRIPTION OF THE DRAWING

FIG. 1 shows the new plant as a 2-year-old in a trial field in full bloom in mid-June in Canby, Oreg.

DETAILED PLANT DESCRIPTION

The following is a detailed description of the new *Penstemon* plant based on observations of two-year-old specimens grown outside in a trial field in full sun in Canby, Oreg. in October. Canby is Zone 8 on the USDA Hardiness map. Temperatures range from a high of 95° F. in August to an average of 32° F. in January. Normal rainfall in Canby is 42.8 inches per year. The color descriptions are based on The Royal Horticultural Society Colour Chart, 5$^{th}$ edition, 2007.

Plant:

*Type.*—Herbaceous perennial.
*Form.*—Upright, branching.
*Cold Hardiness.*—USDA Zone 6-10.
*Size.*—Grows to 41 cm wide and 56 cm tall.
*Vigor.*—Excellent.
*Stem number.*—About 19 main stems from the crown.
*Stem strength.*—Strong.
*Stem.*—Strongly upright, branched with branches strongly upright, grows to 35 cm long to the main inflorescence and 5 mm wide (at the base), glabrous, internodes grow to 4.3 cm long, Yellow Green 146C.

*Roots and rooting.*—Fibrous root system, White 155C, roots easily from stem cuttings in 10 to 14 days.

Leaf:

*Type.*—Simple.

*Arrangement.*—Opposite.

*Shape.*—Lanceolate.

*Venation.*—Pinnate, main vein Yellow Green 145B both sides.

*Margins.*—Serrulate.

*Apex.*—Acute.

*Base.*—Sessile.

*Petiole.*—None, sessile.

*Blade size.*—Grows to 8.5 cm long and 1.7 cm wide.

*Surface texture.*—Glabrous on both sides.

*Leaf color.*—Topside Green N 137D, bottom side closest to Green 137C.

Inflorescence:

*Type.*—Terminal, many flowered, dense thyrse.

*Number of flowers per inflorescence.*—50-60.

*Size of inflorescence.*—Grows to 24.5 cm long and 7 cm wide.

*Peduncle.*—Strong, upright, grows to 5 cm long and 2 mm wide, glandular pubescent, closest to Yellow Green 146C.

*Pedicel.*—Medium strength, grows upright to 0.4 cm long and 1 mm wide, glandular pubescent, Yellow Green 146C tinted Greyed Purple 187A in high light.

*Bloom period.*—Mid-May to frost in November in Canby, Oreg. if spent flowers are removed.

Flower bud:

*Size.*—2.5 cm long and 0.9 cm wide.

*Description.*—Closed tubular, bulging, flattened centrically, pubescent.

*Color.*—Topside of bud closest to Red Purple 61B at tip blending to Red Purple 61C towards base.

Flower:

*Type.*—Zygomorphic, perfect.

*Shape.*—Tubular, bilabiate.

*Size.*—Grows to 3.4 cm long and 2.4 cm wide.

*Corolla description.*—Grows to 3.3 cm long and 2.4 cm wide; tube is bulbous in the calyx for 0.3 cm long and 0.4 cm wide, narrowing then widening for 3.0 cm and flaring to 2.4 cm wide, 5 lobes; top 2 lobes reflexed, tips acute 0.7 cm long and 1 cm wide, 3 bottom lobes, reflexed, tips rounded, 1 cm and 0.8 cm wide; lobe margins entire; outside glandular pubescent, inside sparsely pubescent; topside of flower closest to Red Purple 64C at tip blending to Red Purple 64C tinted with Red Purple 65A, base Red Purple 64A, usually covered by the calyx; inside color Red Purple 64B on lobes outer ¾, ring of White NN155D extends to base of flower.

*Calyx description.*—8 mm deep and 8 mm wide, 5 lobes cut to the base; lobes lanceolate, 8 mm deep and 0.3 cm wide; margins entire; tip acuminate; base cuneate; Greyed Purple 187A at tip blending to Yellow Green 144B at base, outside pubescent, inside glabrous.

*Pistil description.*—1, 2.4 cm long, ovary 0.5 cm long and 1 mm wide, Yellow Green 144C; style 1.9 cm long and less than 1 mm wide, style White NN155C; stigma 0.2 cm flattened, White NN155C.

*Stamen description.*—5, one sterile without an anther, held within the corolla 1.6 cm long; filaments 1.6 cm to 2.1 cm long and less than 1 mm wide, White NN155C; anthers horseshoe-shaped, 2 mm long and 1 mm wide, Black 202 A; pollen amount low, White NN155C.

*Fragrance.*—None.

*Lastingness.*—A flower lasts 5 to 6 days.

Fruit:

*Type.*—Capsule.

*Fertility.*—Poor.

*Size.*—7 mm deep and 5 mm wide.

*Texture.*—Glabrous.

*Color.*—Brown N199C.

Seed:

*Shape.*—Irregular.

*Size.*—1 mm long.

*Texture.*—Glabrous.

*Color.*—Brown 200A.

Pests and diseases: The new plant is typical to the genus. No problems have been found in Canby, Oreg.

I claim:

1. A new and distinct *Penstemon* plant as illustrated and described.

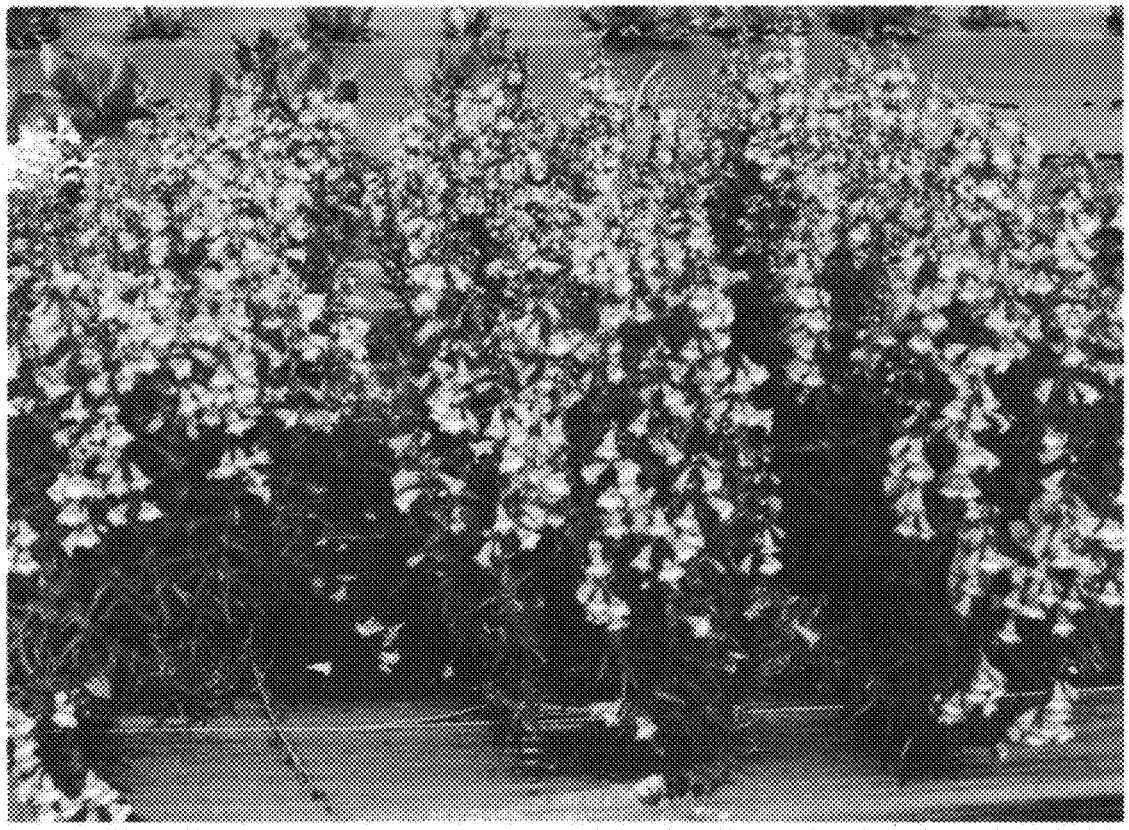

* * * * *